(12) United States Patent
Hu

(10) Patent No.: US 11,709,360 B2
(45) Date of Patent: Jul. 25, 2023

(54) IMAGING METHOD FOR MODULAR MIXED REALITY (MR) DEVICE

(71) Applicant: HOLO INTERACTIVE US, INC., Long Island City, NY (US)

(72) Inventor: Botao Hu, Palo Alto, CA (US)

(73) Assignee: HOLO INTERACTIVE US, INC., Long Island City, NY (US)

(*) Notice: Subject to any disclaimer, the term of this patent is extended or adjusted under 35 U.S.C. 154(b) by 251 days.

(21) Appl. No.: 16/477,527

(22) PCT Filed: Jun. 1, 2018

(86) PCT No.: PCT/CN2018/089434
§ 371 (c)(1),
(2) Date: Jul. 12, 2019

(87) PCT Pub. No.: WO2018/219336
PCT Pub. Date: Dec. 6, 2018

(65) Prior Publication Data
US 2019/0361236 A1 Nov. 28, 2019

(30) Foreign Application Priority Data

Jun. 2, 2017 (CN) .......................... 201710406371.3

(51) Int. Cl.
*G02B 27/01* (2006.01)
*A61B 5/00* (2006.01)
(Continued)

(52) U.S. Cl.
CPC .......... *G02B 27/017* (2013.01); *A61B 5/6803* (2013.01); *G06T 19/006* (2013.01);
(Continued)

(58) Field of Classification Search
CPC . G06F 3/01; G06F 3/011; G06F 3/012; G06F 3/03; G06F 3/0304; G06F 3/0346;
(Continued)

(56) References Cited

U.S. PATENT DOCUMENTS

| 7,513,668 B1 * | 4/2009 | Peng | ................... G02B 27/0103 |
| | | | 362/618 |
| 10,402,663 B1 * | 9/2019 | Tsai | .......................... B60R 1/00 |

(Continued)

FOREIGN PATENT DOCUMENTS

| CN | 104995583 A | 10/2015 |
| CN | 105144030 A | 12/2015 |

(Continued)

OTHER PUBLICATIONS

Taketomi et al., "Visual SLAM algorithms: a survey from 2010 to 2016", IPSJ Transactions on Computer Vision and Applications, (2017) 9:16, published Jun. 2, 2017. (Year: 2017).*

(Continued)

*Primary Examiner* — Keith L Crawley
(74) *Attorney, Agent, or Firm* — Hauptman Ham, LLP

(57) ABSTRACT

An imaging method is provided for a modular mixed reality (MR) device having an MR calculation module, an MR optical path module and an MR posture module. The MR calculation module is configured to adjust display content according to data from the MR posture module. The MR optical path module comprises a virtual-image optical path and a mixed optical path. A semi-transparent semi-reflective mirror is provided in the mixed optical path. One surface of the mirror is a real-image introduction surface facing a real environment, while the other is a virtual-image introduction surface facing the virtual-image optical path. Virtual-image light is reflected by the virtual-image introduction surface onto an observation end and mixed with real environment (Continued)

light transmitted to the observation end by the real-image introduction surface to form a mixed reality image.

19 Claims, 8 Drawing Sheets

(51) Int. Cl.
- *G06T 19/00* (2011.01)
- *G06V 20/20* (2022.01)
- *H04M 1/72409* (2021.01)
- *G06F 3/01* (2006.01)

(52) U.S. Cl.
CPC ...... *G06V 20/20* (2022.01); *H04M 1/724097* (2022.02); *A61B 2503/12* (2013.01); *G02B 2027/014* (2013.01); *G02B 2027/0187* (2013.01); *G06F 3/012* (2013.01)

(58) Field of Classification Search
CPC . G06F 3/04815; G02B 27/0093; G02B 27/01; G02B 27/0101; G02B 27/017; G02B 27/0172; G02B 27/0176; G02B 27/0179; G02B 2027/0138; G02B 2027/014; G02B 2027/015; G02B 2027/0152; G02B 2027/0161; G02B 2027/0187; G06T 7/70; G06T 7/74; G06T 19/006; G06T 2207/30244; A61B 5/6803; G06K 9/00671

See application file for complete search history.

(56) References Cited

U.S. PATENT DOCUMENTS

| | | | | |
|---|---|---|---|---|
| 2008/0030461 | A1* | 2/2008 | Matsui | G06F 3/011 |
| | | | | 345/156 |
| 2014/0168261 | A1* | 6/2014 | Margolis | A63F 13/65 |
| | | | | 345/633 |
| 2016/0216760 | A1 | 7/2016 | Trutna et al. | |
| 2017/0212352 | A1* | 7/2017 | Cobb | G02B 27/0179 |
| 2017/0336511 | A1* | 11/2017 | Nerurkar | H04N 13/271 |
| 2018/0188383 | A1* | 7/2018 | Niesen | G01C 22/00 |
| 2018/0315209 | A1* | 11/2018 | Murphy-Chutorian | G06K 9/00664 |
| 2019/0178654 | A1* | 6/2019 | Hare | G06T 7/70 |

FOREIGN PATENT DOCUMENTS

| | | |
|---|---|---|
| CN | 206115040 U | 4/2017 |
| CN | 106610527 A | 5/2017 |
| CN | 107065195 A | 8/2017 |

OTHER PUBLICATIONS

"Aryzon—3D Augmented Reality for Your Smartphone" Kickstarter Campaign, Slaa, Maarten et al., published May 29, 2017 [retrieved Jul. 13, 2021]; Retrieved from the internet <URL: https://www.kickstarter.com/projects/aryzon/aryzon-3d-augmented-reality-for-every-smartphone> (Year: 2017).*

Printout of "Aryzon—3D Augmented Reality for Your Smartphone" Kickstarter Campaign, Slaa, Maarten et al., published May 29, 2017; Retrieved from the internet <URL: https://www.kickstarter.com/projects/aryzon/aryzon-3d-augmented-reality-for-every-smartphone> (Year: 2017).*

International Search Report for PCT/CN2018/089434 dated Sep. 7, 2018.

Written Opinion of International Searching Authority dated Sep. 7, 2018.

* cited by examiner

IMAGING METHOD FOR MODULAR MIXED REALITY (MR) DEVICE

CROSS-REFERENCE TO RELATED APPLICATION

This application is a National Stage Application under 35 U.S.C. §371 and claims the benefit of International Application No. PCT/CN2018/089434, and claims priority to Chinese Patent Application No. 201710406371.3, filed on Jun. 2, 2017, the disclosure of which are hereby incorporated by reference in its entirety.

TECHNICAL FIELD

The present invention relates to the field of display devices, more specifically, to an imaging method for a modular mixed reality (MR) device.

BACKGROUND

The present MR device is a display device that can superimpose virtual-images onto a real environment background. In the past, such devices are usually composed of high-performance computing devices and complicated optical paths and are costly and inconvenient to use. The present portable virtual reality (VR) glasses utilize a popularized mobile phone as the core of display, significantly reducing the cost of forming a virtual reality image and making the use more convenient.

SUMMARY

How to apply the display principle of the portable VR glasses to an MR device to significantly reduce the cost of the MR device is the technical problem to be solved by the present invention.

Technical Solution

The present invention provides a modular MR device imaging method which can produce an inexpensive MR device and can flexibly render rich MR interaction effects.

The present invention employs the following technical solutions.

A modular MR device imaging method, the MR device comprises an MR calculation module, an MR optical path module and an MR posture module; the MR calculation module comprises a display assembly; the MR posture module comprises an imaging assembly and an IMU assembly; the imaging assembly is configured to acquire image data in a preset angular direction of the display assembly; the IMU assembly is configured to collect posture data of the MR device; the MR calculation module is connected to the MR posture module, adjusting display content of the display assembly according to the image data and posture data acquired by the MR posture module;

The MR optical path module comprises a virtual-image optical path and a mixed optical path; the virtual-image optical path is connected to the display assembly; the input end of the mixed optical path is connected to the virtual-image optical path, while the output end is an observation end; a semi-transparent semi-reflective mirror is provided in the mixed optical path, one surface of the semi-transparent semi-reflective mirror is the real-image introduction surface, the other surface of the mirror is the virtual-image introduction surface; the real-image introduction surface faces a real environment, while the virtual-image introduction surface faces the virtual-image optical path; the display content of the display assembly is processed and transmitted by means of the virtual-image optical path to form virtual image; the virtual-image light is reflected by means of the virtual-image introduction surface onto the observation end, and real environment light is transmitted through to the observation end by means of the real-image introduction surface, being mixed with the virtual image to form a mixed reality image.

The MR calculation module is the main smart phone; the display assembly is the display module of the main smart phone; the IMU assembly comprises a magnetometer, a gyroscope and an accelerometer; the IMU assembly is composed of a main IMU assembly and an auxiliary IMU assembly. The main IMU assembly collects the posture data of the display assembly and is configured in the main smart phone. The auxiliary IMU assembly is configured in one or more control devices wirelessly connected to the main smart phone; the auxiliary IMU assembly collects the posture data or position data of the one or more control devices; the posture data includes posture angle, angular rate or acceleration data; the imaging assembly comprises a main imaging assembly and an auxiliary imaging assembly; the main imaging assembly is the rear camera of the main smart phone, and the auxiliary imaging assembly is the camera placed at the control device The MR optical path module is a passive MR head-mounted mechanism; the main smart phone is fixed at the MR head-mounted mechanism; the main imaging assembly is the rear camera of the main smart phone; the control device is either a game controller, a wearable device that can be worn on the hand or the foot, a sensor and a control device that are fixed at the MR head-mounted mechanism, or an auxiliary phone that is held by a user or is tied to the limbs of the user.

The virtual-image optical path of the MR head-mounted mechanism comprises a resting plate, a total reflection mirror and a field lens; the field lens is composed of two Fresnel lenses; the main smart phone is placed horizontally on the resting plate. While the MR head-mounted mechanism is in operation, the main smart phone displays VR split-screen mode image in the form of horizontal double-split screen; the image light of the double-split screen is reflected through the total reflection mirror onto the two Fresnel lenses, which then refract image light of double-split screen, so that image light forms two virtual-image light paths with preset field angle. Virtual-image light is reflected via the virtual-image introduction surface onto the observation end, and real environment light is transmitted to the observation end through the real-image introduction surface, being mixed with the virtual image light to form a mixed reality image.

The orientation of the rear camera of the main smart phone is the orientation of the MR head-mounted mechanism; the posture data of the display assembly is the posture data of the main smart phone; the IMU assembly at the main smart phone collects the posture data of the main smart phone; when the MR head-mounted mechanism is in operation, the rear camera of the main smart phone collects feature points of the real scene at the initial orientation of the MR head-mounted mechanism, and successively collects images as posture images while the MR head-mounted mechanism is in operation; the MR calculation module adjusts the images on the double-split screen according to the variation of the feature points at the posture image and the variation of the posture data of the main smart phone.

The image displayed in the form of horizontal double-split screen comprises a virtual character and a control identifier; the MR calculation module generates the control identifier according to the posture data and the position data of the control device uploaded by the auxiliary IMU assembly; the control identifier moves with the movement of the control device; the virtual character can interact with the control identifier.

The main smart phone is connected to an external device by network; the virtual character and the control identifier included in the image that is displayed in the form of horizontal double-split screen is a part of the mixed reality image; the virtual character corresponds to the external device, and when the virtual character interacts with the control identifier, the external device performs respective implementation according to the interaction content.

The imaging method sequentially includes the steps of:

A1, the user fixing the main smart phone preinstalled with the MR application to the resting plate of the MR head-mounted mechanism and holding the auxiliary phone which is also a smart phone preinstalled with the MR application;

A2, the user wearing the MR head-mounted mechanism, and bringing the eyes close to the observation end to observe the mixed reality image;

A3, activating the MR application of the main smart phone and setting it as a display end; the main smart phone displaying the image in the form of horizontal double-split screen, image light of double-split screen is reflected by means of the total reflection mirror onto the two Fresnel lenses, two Fresnel lenses refract image light of double-split screen, so that image light forms two virtual-image light paths with preset field angle; virtual-image light is reflected by means of the virtual-image introduction surface onto an observation end, and real environment light transmitted to the observation end by means of the real-image introduction surface, being mixed with the virtual image light to form a mixed reality image;

A4, the rear camera of the main smart phone collecting feature points of the real scene at the initial orientation of the MR head-mounted mechanism, and successively collecting images as posture images while the MR head-mounted mechanism is in operation; the MR calculation module is configured to adjust the images on the double-split screen according to the variation of the feature points at the posture image and the variation of the posture data of the main smart phone;

A5, the user lifting the auxiliary mobile phone to a specific point of the mixed reality image, activating the MR application on the auxiliary phone, and setting it as a control end; the auxiliary IMU assembly on the auxiliary phone is configured to collect the posture data and the position data of the auxiliary phone; the control end is configured to upload the posture data and position data of the auxiliary phone to the display end which is connected to the control end wirelessly;

A6, the MR calculation module is configured to generate the control identifier on the mixed reality image according to the posture data and position data of the auxiliary phone, wherein the control identifier moves with the movement of the auxiliary phone; when the control identifier on the mixed reality image is in contact with or adjacent to the virtual character, the virtual character interacts with the control identifier;

A7, the virtual character corresponds to the external device, and when the virtual character is interacting with the control identifier, the external device performs the corresponding implementation according to the interaction content.

The main smart phone and the auxiliary phone generate and share unified spatial locating data by monocular visual inertial odometer method, the monocular visual inertial odometer method comprising the steps of;

B1, the main smart phone and the auxiliary phone are configured to collect images by means of cameras which generate posture image respectively; the main smart phone and the auxiliary phone are configured to collect posture data by means of built-in IMU assembly respectively; the main smart phone and the auxiliary phone associate the posture image with the posture data respectively, forming a respective spatial image association data; the main smart phone and the auxiliary phone aggregate respective spatial image related data through network connection to generate an unified spatial image related database in the main smart phone and the auxiliary phone;

B2, the main smart phone and the auxiliary phone successively collect posture images and posture data during the movement, and add the collected posture images and posture data to the spatial image related database respectively to associate;

B3, during the movement, the main smart phone and the auxiliary phone compare the collected posture images and the posture data with that data in the spatial image related database to obtain the exact location of the phone in the current space and predict the trajectory and posture change of the phone;

B4, the main smart phone and the auxiliary phone read the spatial image related database during the movement, and compare the collected posture images with the posture images and the posture data in the past N time frames collected from the same coordinate and same posture, update the spatial image related database when there is difference between the collected posture images and the posture images and the posture data in the past N time frames;

B5, in steps B3 and B4, the main smart phone and the auxiliary phone compare and verify the data with a preset tolerance threshold to improve the efficiency and robustness of the spatial location.

The MR head-mounted mechanism is made up of a sheet, which is provided with an A-folding section, a B-folding section and a C-folding section along the length; the A-folding section is fixed with the semi-transparent and semi-reflective mirror and the field lens; the B-folding section is fixed with the total reflective mirror; the C-folding section is provided with resting plate; the resting plate is provided with a observation hole for collecting external images by the rear camera of the main smart phone.

The method for preparing the MR head-mounted mechanism comprises the steps of:

B1, folding the A-folding section and the B-folding section to a rhombic column, so that the lens is located at the connection line of the rhombic vertex; one side surface of the rhombic column is open and is an incident surface of image light, and the other three side surfaces are closed and form an observation hole wall, a semi-transparent semi-reflective mirror wall and a total reflective mirror wall respectively; the incident surface of image light faces the total reflective mirror wall; the total reflective mirror wall is provided with the total reflective mirror; the observation hole locates at the observation hole wall; the side wall of the rhombic column facing the observation hole is the semi-transparent semi-reflective mirror; the semi-transparent semi-reflective mirror locates at the semi-transparent semi-reflective mirror wall;

B2, expanding a light shield at the A-folding section and inserting the light shield into the observation hole wall;

B3, expanding the C-folding section and putting the main smart phone having rear camera on the resting plate, so that the rear camera aligns to the observation hole of the resting plate; folding the C-folding section then to the incident surface of light image of the rhombic column; the observation end includes the observation hole, at which the mixed reality image formed by mixing the screen image of the phone with the external image can be seen when the main smart phone displays the VR split screen mode image in the form of horizontal double-split screen.

The bottom of the resting plate is configured with a damper; the resting plate is detachably coupled to the housing via velcro tapes or buckles; the resting plate is fixedly coupled to the housing.

The MR calculation module is the main smart phone; the display assembly is the display module of the main smart phone; the IMU assembly comprises a magnetometer, a gyroscope and an accelerometer; the IMU assembly is composed of a main IMU assembly and zero or more auxiliary IMU assemblies; the main IMU assembly collects the posture data of the display assembly and is configured in the main smart phone; the auxiliary IMU assembly is arranged in one or more control devices wirelessly connected to the main smart phone; the auxiliary IMU assembly collects the posture data or position data of the one or more control devices; the posture data includes posture angle, angular rate or acceleration data; the imaging assembly comprises a main imaging assembly and an auxiliary imaging assembly; the main imaging assembly is a rear camera of the main smart phone, and the auxiliary imaging assembly is a camera at the control device and is optional.

The MR optical path module is a passive MR head-mounted mechanism; the main smart phone is fixed at the MR head-mounted mechanism; the main imaging assembly is the rear camera of the main smart phone; the control device is either a game console handle, a wearable device that can be worn on the hand or the foot, a sensor and a control device that are fixed at the MR head-mounted mechanism, or an auxiliary phone that is held by the user or is tied to the limbs of the user.

The virtual-image optical path of the MR head-mounted mechanism comprises a resting plate, a total reflection mirror and a field lens; the field lens is combined by two Fresnel lenses; the main smart phone is placed horizontally on the resting plate; the main smart phone displays the VR split-screen mode image in the form of double-split screen in the transverse direction when the MR head-mounted mechanism is in operation; image light of double-split screen is reflected by means of the total reflection mirror onto the two Fresnel lenses, which then refract image light of double-split screen, so that image light forms two virtual-image light paths with preset field angle; virtual-image light is reflected by means of the virtual-image introduction surface onto an observation end, and real environment light is transmitted to the observation end by means of the real-image introduction surface, being mixed with the virtual image light to form a mixed reality image.

The orientation of the rear camera of the main smart phone is the orientation of the MR head-mounted mechanism; the posture data of the display assembly is the posture data of the main smart phone; the IMU assembly at the main smart phone collects the posture data of the main smart phone; when the MR head-mounted mechanism is in operation, the rear camera of the main smart phone collects feature points of the real scene at the initial orientation of the MR head-mounted mechanism, and successively collects images as posture images of feature points while the MR head-mounted mechanism is in operation; the MR calculation module calculates the space position of the main smart phone according to the variation of the feature points at the posture image and the variation of the posture data of the main smart phone, and adjusts the images on the double-split screen based on the space position.

The image displayed in the form of horizontal double-split screen comprises a virtual character and a control identifier; the MR calculation module generates the space position of the control identifier according to the posture data and position data of the control device uploaded by the auxiliary IMU assembly or the auxiliary imaging assembly; the control identifier moves with the movement of the control device; the virtual character can interact with the control identifier.

The main smart phone is connected to an external device by network; the virtual character and the control identifier included in the image that is displayed in the form of horizontal double-split screen is a part of the mixed reality image; the virtual character corresponds to the external device, and when the virtual character interacts with the control identifier, the external device performs respective implementation according to the interaction content.

The imaging method sequentially includes the steps of:

A1, the user fixes the main smart phone preinstalled with the MR application to the resting plate of the MR head-mounted mechanism and holds the auxiliary phone which is also a smart phone preloaded the MR application;

A2, the user wears the MR head-mounted mechanism, and brings the eyes close to the observation end so as to observe the mixed reality image;

A3, activating the MR application of the main smart phone and setting it as a display end; the main smart phone displays the image in the form of horizontal double-split screen, image light of double-split screen is reflected by means of the total reflection mirror onto the two Fresnel lenses, two Fresnel lenses refract image light of double-split screen, so that image light forms two virtual-image light paths with preset field angle; virtual-image light is reflected by means of the virtual-image introduction surface onto an observation end, and real environment light transmitted to the observation end by means of the real-image introduction surface, being mixed with the virtual image light to form a mixed reality image;

A4, the rear camera of the main smart phone collects feature points of the real scene at the initial orientation of the MR head-mounted mechanism, and successively collects images as posture images of feature points while the MR head-mounted mechanism is in operation; the MR calculation module calculates the space position of the main smart phone according to the variation of the feature points at the posture image and the variation of the posture data of the main smart phone, and adjusts the images on the double-split screen based on the space position;

A5, the user lifts the control device to a specific point of the mixed reality image, if the control device is a smart phone, activates the MR application on the auxiliary phone, and sets it as a control end; the auxiliary IMU assembly on the control device collects the posture data and position data of the auxiliary phone; the control end uploads the posture data and position data of the control device to the display end which is connected to the control end wirelessly;

A6, the MR calculation module generates the control identifier on the mixed reality image according to the posture data and position data of the auxiliary phone, wherein the control identifier moves with the movement of the auxiliary phone; when the control identifier on the mixed reality image is in contact with or adjacent to the virtual character, the virtual character interacts with the control identifier;

A7, the virtual character corresponds to the external device, and when the virtual character is interacting with the control identifier, the external device performs the corresponding implementation according to the interaction content.

The MR head-mounted mechanism is composed of a thin sheet, which is provided with an A-folding section, a B-folding section and a C-folding section along the length; the A-folding section is fixed with the semi-transparent and semi-reflective mirror and the field lens; the B-folding section is fixed with the total reflective mirror; the C-folding section is provided with the resting plate; the resting plate is configured with an observation hole for collecting external images by the rear camera of the main smart phone.

The method for preparing the MR head-mounted mechanism comprises the steps of:

B1, folding the A-folding section and the B-folding section to a rhombic column, so that the lens is located at the connection line of the rhombic vertex; one side surface of the rhombic column is open and is an incident surface of image light, and the other three side surfaces are closed and form an observation hole wall, a semi-transparent semi-reflective mirror wall and a total reflective mirror wall respectively; the incident surface of image light faces the total reflective mirror wall; the total reflective mirror wall is provided with the total reflective mirror; the observation hole locates at the observation hole wall; the side wall of the rhombic column facing the observation hole is the semi-transparent semi-reflective mirror; the semi-transparent semi-reflective mirror locates at the semi-transparent semi-reflective mirror wall;

B2, expanding a light shield at the A-folding section and inserting the light shield into the observation hole wall;

B3, expanding the C-folding section and putting the main smart phone having rear camera on the resting plate, so that the rear camera aligns to the observation hole of the resting plate; folding the C-folding section then to the incident surface of light image of the rhombic column; the observation end includes the observation hole, at which the mixed reality image formed by mixing the screen image of the phone with the external image can be seen when the main smart phone displays the VR split screen mode image in the form of horizontal double-split screen.

Advantageous Effects of the Invention

The present invention adopts a modular design, and the optical path of the MR device is independent of the playing source. The device can be used as long as the displaying capability of the mobile phone which functions as the playing source conforms to the compatible range of the optical path of the MR head-mounted mechanism. The MR head-mounted mechanism housing can be configured without an electronic equipment or equipped with only a few sensors matching the smart phone, thereby greatly reducing the manufacturing cost of the MR glasses.

In the present invention, because the virtual video source of the MR device is a smart phone which is placed within the MR device resting plate as a part of the MR device when the MR device is used, the interactive function of the MR device can be improved with the upgrades of the smart phone hardware and the software performance. Furthermore, the MR device functionality can be upgraded by upgrading the hardware phone or simply updating the phone applications internally, avoiding the need of traditional MR devices to be bind with a device supplier and allowing the upgrading process to be more convenient and economical. For example, when the smart phone is equipped with magnetometer, gyroscope, and accelerometer sensors, if the smart phone can function with these sensors through by using the application of the MR display, the position of the mixed reality image can be displayed. The virtual image of the mixed reality image interacts with the orientation and movement of the MR device, and when the functionality and collecting performance of the IMU assemblies are improved, the functionality of the MR device is also improved.

In the present invention, since the optical path portion of the MR device is composed of folding a thin sheet, different materials can be used for the optical path substrate to meet the various market demands for the price and strength of the MR glasses.

In the present invention, the resting plate is configured with observation hole through which the rear camera of the image player can collect external images; the image player is a smart phone; because the shooting direction of the smart phone's camera is the same as the actual viewing direction of the MR device, the actual viewing direction of the MR device is the direction of the observation hole. This present design enables the interaction between the virtual images of the MR device and the external images captured by the phone camera. Because the images captured by the phone camera are substantially the same as the real image viewed through the observation hole, when the virtual images interact with the real images, the MR display application in the smart phone enables the virtual images to interact correspondingly. For example, if the MR display application in the smart phone displays a kettle as the virtual image, and when the observation hole of the MR device faces a fire, the smart phone camera collects and transmits the fire image to the MR display application, the application then automatically converts the kettle to a kettle with boiling water in the virtual image.

In the present invention, since the displaying smart phone and the controlling smart phone are two independent devices connected by wireless, the controllability the MR device is greatly expandable. Simply installing the corresponding MR application onto the controlling smart phone or game consoles will allow the virtual display on the mixed reality images of various control identifiers, such as a game gun, a shield, a grab, a mechanical arm, or other file control icons.

In the present invention, since the displaying smart phone and the controlling smart phone or the game consoles are independent devices connected by wireless, the controllability of the MR device is greatly expandable. Simply installing the corresponding MR application onto the controlling smart phone or game consoles will allow the virtual display on the mixed reality images of various control identifiers, such as a game gun, a shield, a grab, a mechanical arm, or other file control icons.

Since the optical path module of the present MR device is composed of folding a thin sheet, the cost is extremely low. Additionally, with the computing and controlling device being a software-installable smart phone, users can obtain the various modules of the MR device at a low cost. Through the setting function of application on the smart phone, the MR device can be figured to fully integrate with the office or home setting thus greatly improving the utility of the MR device. For example, after the user wears the MR head-mounted mechanism, he virtually controls the file control icons through the handheld smart phone, reviews the manuscript in mixed reality state, and finalizes it for printing. The user then can maneuver and move the file control icon directly onto the virtual printer icon in mixed reality state. Because the virtual printer icon is assigned to a real printer, the interaction of the file control icon with the virtual printer icon is equivalent to sending the printing command, and the real printer performs the printing command directly.

BRIEF DESCRIPTION OF THE DRAWINGS

The present invention will be further described in detail below with reference to the accompanying drawings and specific embodiments.

In the Figures: 1—MR optical path module; 2—total reflection mirror; 3—field lens; 4—semi-transparent semi-reflective mirror; 5—resting plate; 6—light shield; 601—observation end; 7—damper; a—MR calculation module;

101—Fresnel lens; 102—observation hole; 103—C folded section; 104—A folded section; 105—B folded section; 106—main smart phone; 107—control identifier; 108—virtual character; 109—display assembly.

DETAILED DESCRIPTIONS

Best Embodiments

Figure 1:
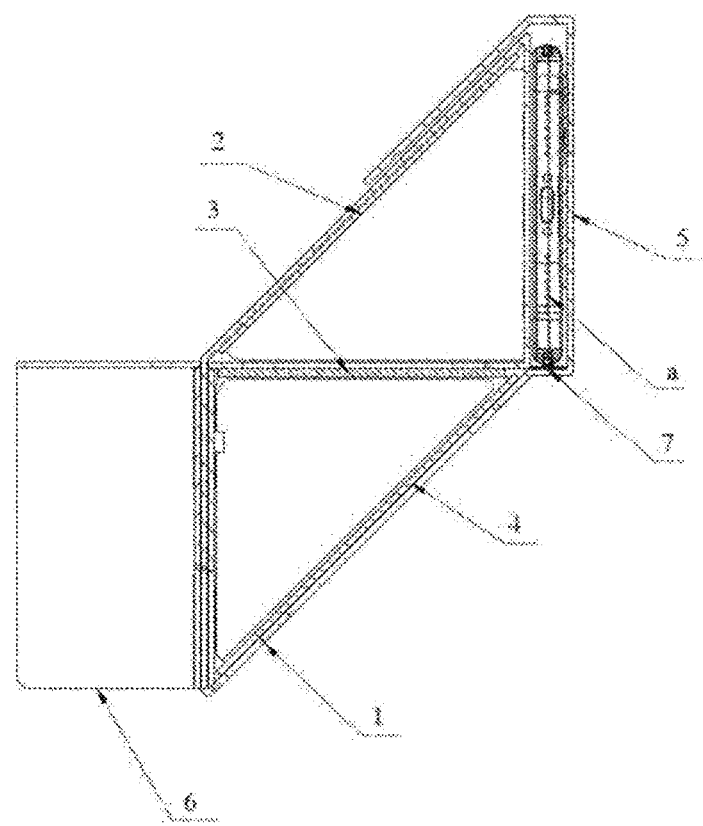
FIG. 1 is a schematic diagram of the present invention.
Figure 2:
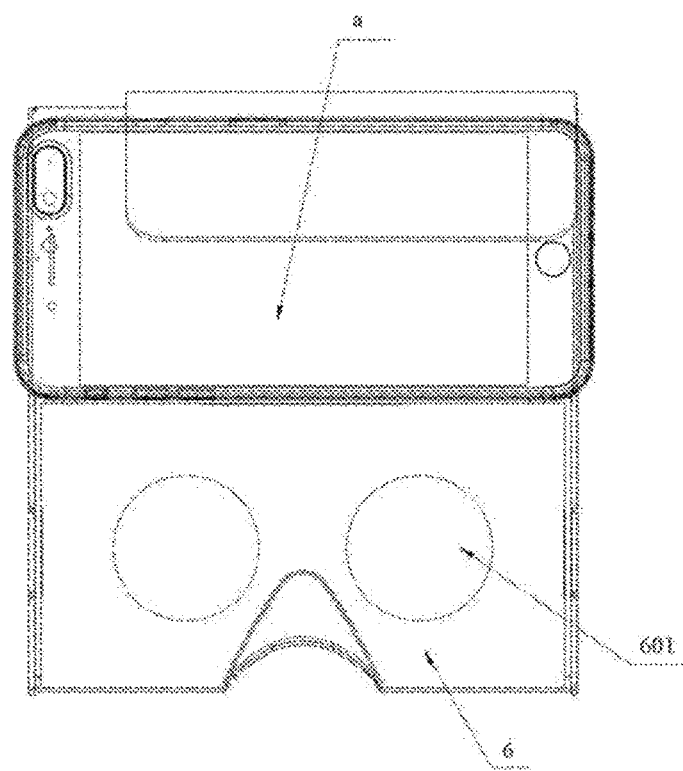
FIG. 2 is a schematic diagram of the present invention shown in another direction.
Figure 3:
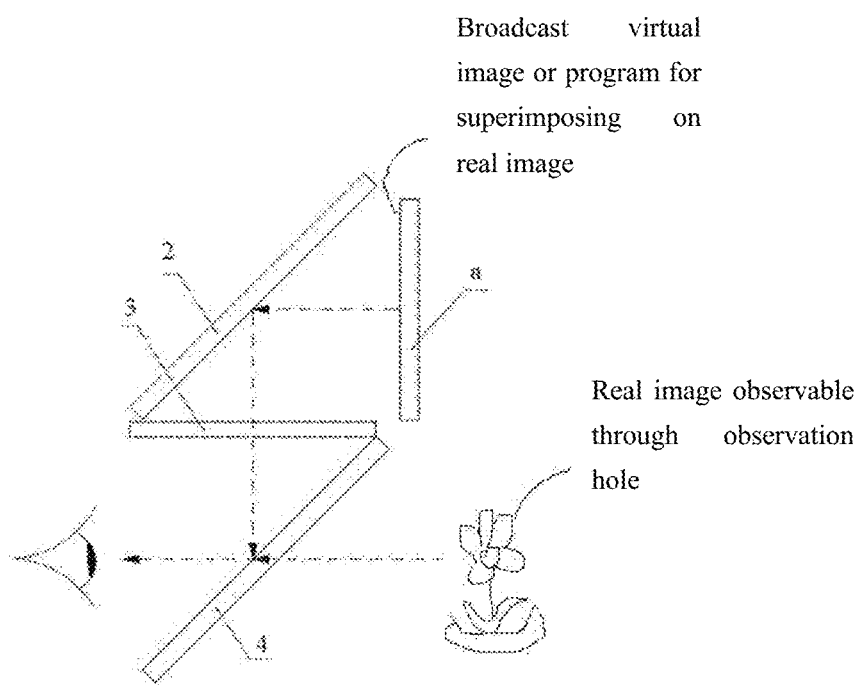
FIG. 3 is a schematic diagram of an optical path of the present invention.
Figure 4:
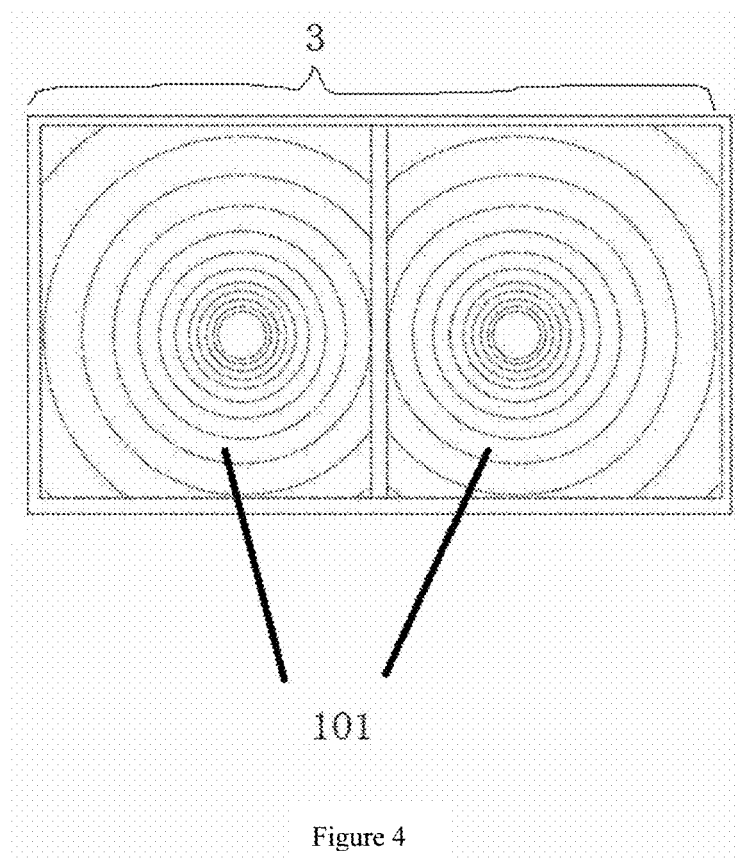
FIG. 4 is a schematic structure diagram of a lens of the present invention.
Figure 5:
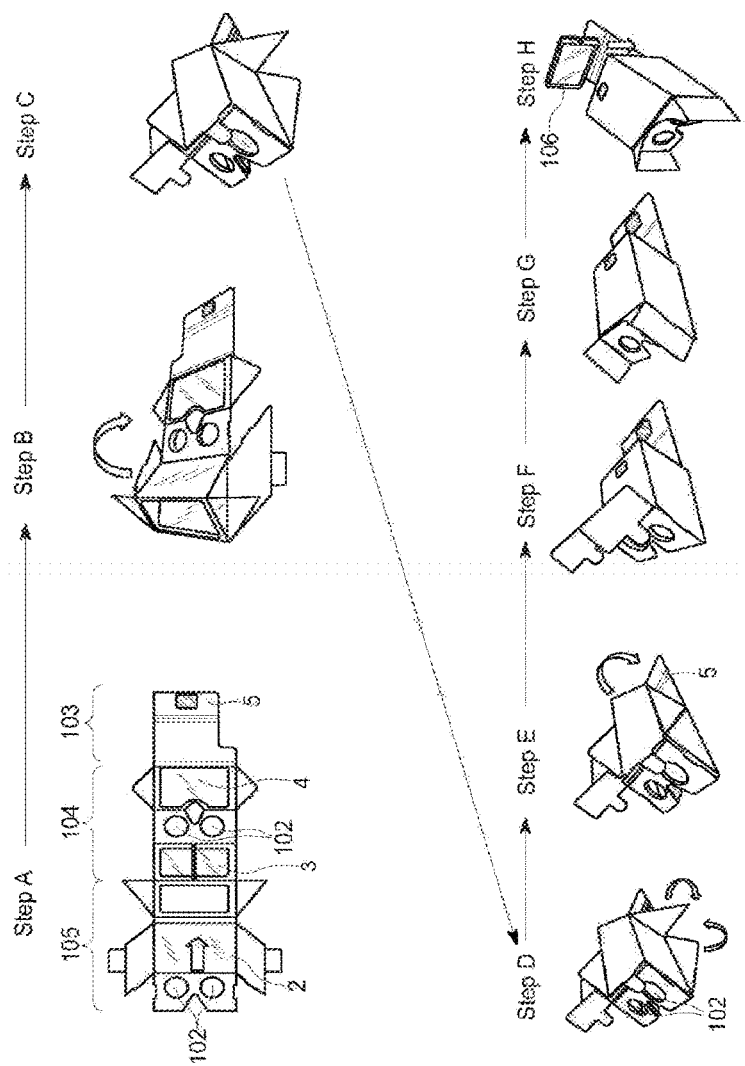
FIG. 5 is a schematic diagram showing a folding process of a housing of the present invention.
Figure 6:
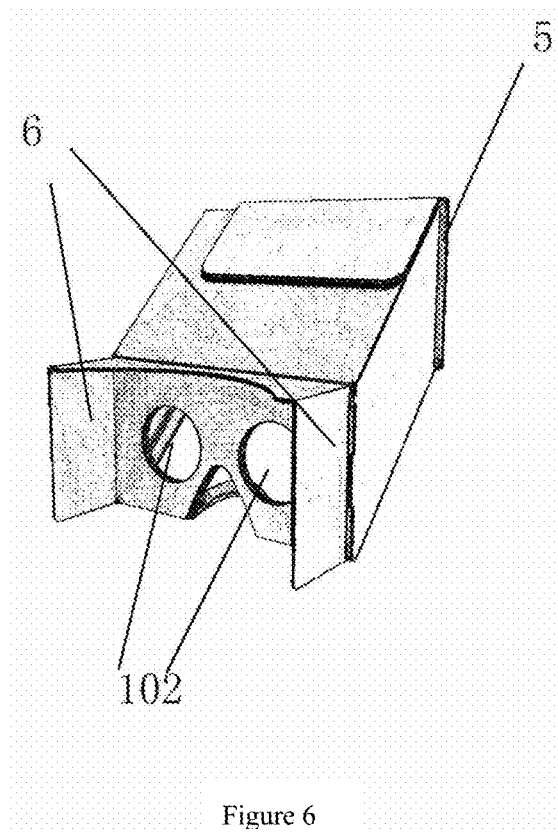
FIG. 6 is a perspective view of the present invention.
Figure 7:
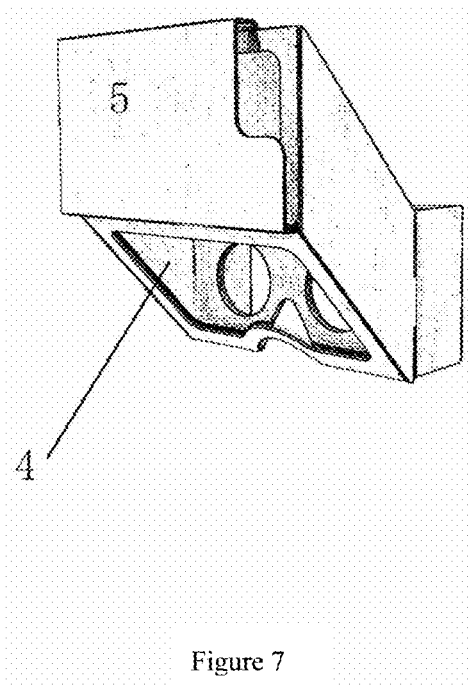
FIG. 7 is another perspective view of the present invention.
Figure 8:
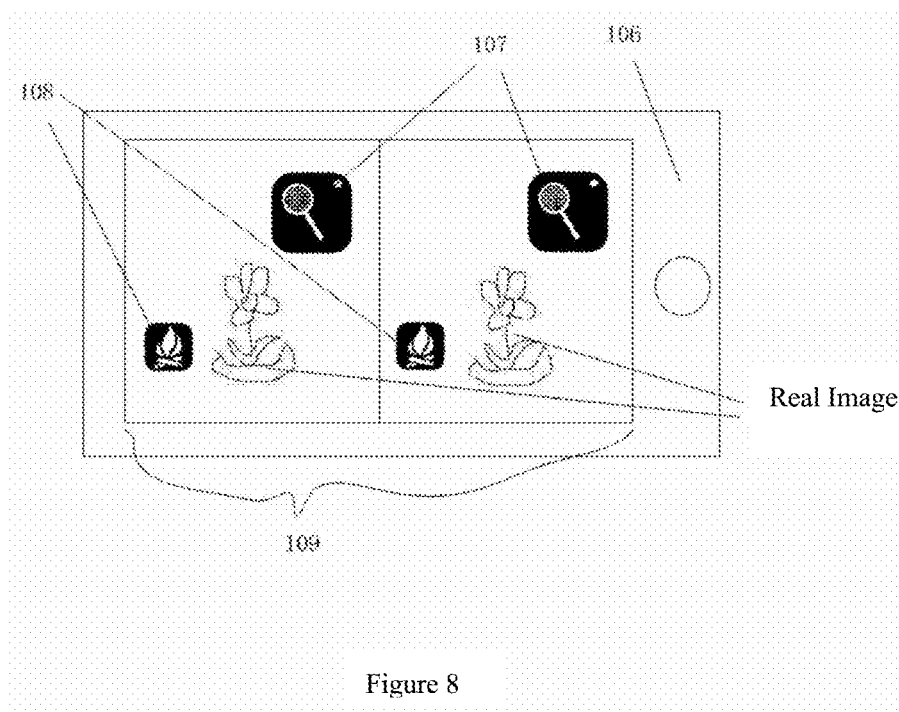
FIG. 8 is a schematic diagram showing a main smart phone playing images in a VR split-screen mode in the form of a horizontal double-split screen according to the present invention.

FIGS. 1-8 illustrate an imaging method for a modular MR device. The MR device comprises: an MR calculation module a, an MR optical path module 1 and an MR posture module; the MR calculation module a comprises a display assembly 109; the MR posture module comprises an imaging assembly and an IMU assembly, and the imaging assembly is configured to collect images on the display assembly in a preset angular direction of the display assembly, and the IMU assembly is configured to collect posture data of the MR device; the MR calculation module is connected to the MR posture module, adjusting display content of the display assembly according to the image data and the posture data acquired by the MR posture module.

The MR optical path module 1 comprises a virtual-image optical path and a mixed optical path; the virtual-image optical path is connected to the display assembly; the input end of the mixed optical path is connected to the virtual-image optical path, while the output end thereof is an observation end; a semi-transparent semi-reflective mirror 4 is configured on the mixed optical path; the semi-transparent semi-reflective mirror 4 is configured with a real-image introduction on one surface and a virtual-image introduction on the other surface; the real-image introduction surface faces a real environment, while the virtual-image introduction surface faces the virtual-image optical path; display content of the display assembly is processed by means of the virtual-image optical path and is transmitted to form a virtual image; virtual-image light is reflected by means of the virtual-image introduction surface onto an observation end, and real environment light is transmitted to the observation end 601 by means of the real-image introduction surface, being mixed with the virtual image to form a mixed reality image.

The MR calculation module is a main smart phone 106; the display assembly is a display module of the main smart phone 106; the IMU assembly comprises a magnetometer, a gyroscope and an accelerometer; the IMU assembly comprises a main IMU assembly and an auxiliary IMU assembly; the main IMU assembly collects the posture data of the display assembly and is configured in the main smart phone; the auxiliary IMU assembly is configured at one or more control devices wirelessly connected to the main smart phone; the auxiliary IMU assembly collects the posture data or position data of the one or more control devices; the posture data includes posture angle, angular rate or acceleration data; the imaging assembly comprises a main imaging assembly and an auxiliary imaging assembly; the main imaging assembly is a rear camera of the main smart phone, and the auxiliary imaging assembly is a camera configured at the control devices.

The MR optical path module 1 is a passive MR head-mounted mechanism; the main smart phone 106 is fixed at the MR head-mounted mechanism 1; the main imaging assembly is the rear camera of the main smart phone; the control device is either a game console handle, a wearable device that can be worn on the hand or the foot, a sensor and a control device that are fixed at the MR head-mounted mechanism, or an auxiliary phone that is held by a user or is tied to the limbs of the user.

The virtual-image optical path of the MR head-mounted mechanism comprises a resting plate 5, a total reflection mirror 2 and a field lens 3; the field lens 3 is composed of two Fresnel lenses 10; the main smart phone 106 is placed horizontally on the resting plate 5. While the MR head-mounted mechanism is in operation, the main smart phone displays the VR split-screen mode image in the form of horizontal double-split screen; the image light of double-split screen is reflected through the total reflection mirror onto the two Fresnel lenses, which then refract image light of double-split screen, so that image light forms two virtual-image light paths with preset field angle; virtual-image light is reflected via the virtual-image introduction surface onto an observation end, and real environment light is transmitted to the observation end through the real-image introduction surface, being mixed with the virtual image light to form a mixed reality image.

The orientation of the rear camera of the main smart phone is the orientation of the MR head-mounted mechanism; the posture data of the display assembly is the posture data of the main smart phone 106; the IMU assembly at the main smart phone collects the posture data of the main smart phone; when the MR head-mounted mechanism is in operation, the rear camera of the main smart phone collects feature points of the real scene at the initial orientation of the MR head-mounted mechanism, and successively collects images as posture images while the MR head-mounted mechanism is in operation; the MR calculation module adjusts the images on the double-split screen according to the variation of the feature points at the posture image and the variation of the posture data of the main smart phone.

The image displayed in the form of transverse double-split screen comprises a virtual character 108 and a control identifier 107; the MR calculation module generates the control identifier according to the posture data and the position data of the control device uploaded by the auxiliary IMU assembly; the control identifier moves with the movement of the control device; the virtual character can interact with the control identifier.

The main smart phone is connected to an external device by network; the virtual character and the control identifier included in the image that is displayed in the form of transverse double-split screen is a part of the mixed reality image; the virtual character corresponds to the external device, and when the virtual character interacts with the control identifier, the external device performs respective implementation according to the interaction content.

The imaging method sequentially includes the steps of:

A1, the user fixing the main smart phone 106 preinstalled with the MR application to the resting plate of the MR head-mounted mechanism and holding the auxiliary phone which is also a smart phone preloaded the MR application;

A2, the user wears the MR head-mounted mechanism, and brings the eyes close to the observation end so as to observe the mixed reality image;

A3, activating the MR application of the main smart phone and setting it as a display end; the main smart phone displays the image in the form of transverse double-split screen, image light of double-split screen is reflected by means of the total reflection mirror onto the two Fresnel lenses, two Fresnel lenses refract image light of double-split screen, so that image light forms two virtual-image light paths with preset field angle; virtual-image light is reflected by means of the virtual-image introduction surface onto an observation end, and real environment light transmitted to the observation end by means of the real-image introduction surface, being mixed with the virtual image light to form a mixed reality image;

A4, the rear camera of the main smart phone collects feature points of the real scene at the initial orientation of the MR head-mounted mechanism, and successively collects images as posture images while the MR head-mounted mechanism is in operation; the MR calculation module adjusts the images on the double-split screen according to the variation of the feature points at the posture image and the variation of the posture data of the main smart phone;

A5, the user lifts the auxiliary mobile phone to a specific point of the mixed reality image, activates the MR application on the auxiliary phone, and sets it as a control end; the auxiliary IMU assembly on the auxiliary phone collects the posture data and the position data of the auxiliary phone; the control end uploads the posture data and position data of the auxiliary phone to the display end which is connected to the control end wirelessly;

A6, the MR calculation module generates the control identifier on the mixed reality image according to the posture data and position data of the auxiliary phone, wherein the control identifier moves with the movement of the auxiliary phone; when the control identifier on the mixed reality image is in contact with or adjacent to the virtual character, the virtual character interacts with the control identifier;

A7, the virtual character corresponds to the external device, and when the virtual character is interacting with the control identifier, the external device performs the corresponding implementation according to the interaction content.

The main smart phone and the auxiliary phone generate and share unified spatial locating data by monocular visual inertial odometer method, the monocular visual inertial odometer method comprising the steps of:

B1, the main smart phone and the auxiliary phone are configured to collect images by means of cameras to generate posture image respectively; the main smart phone and the auxiliary phone collect posture data by means of built-in IMU assembly respectively; the main smart phone and the auxiliary phone associate the posture image with the posture data respectively, forming a respective spatial image association data; the main smart phone and the auxiliary phone aggregate respective spatial image related data through network connection to generate a unified spatial image related database in the main smart phone and the auxiliary phone;

B2, the main smart phone and the auxiliary phone successively collect posture images and posture data during the movement, and add the collected posture images and posture data to the spatial image related database respectively to associate;

B3, during the movement, the main smart phone and the auxiliary phone compare the collected posture images and the posture data with that data in the spatial image related database to obtain the exact location of the phone in the current space and predict the trajectory and posture change of the phone;

B4, the main smart phone and the auxiliary phone read the spatial image related database during the movement, and compare the collected posture images with the posture images and the posture data in the past N time frames collected from the same coordinate and same posture, updating the spatial image related database when there is difference between the collected posture images and the posture images and the posture data in the past N time frames;

B5, in steps B3 and B4, the main smart phone and the auxiliary phone compare and verify the data with a preset tolerance threshold to improve the efficiency and robustness of the spatial location.

The MR head-mounted mechanism is made up of a sheet, which is provided with an A-folding section 104, a B-folding section 105 and a C-folding section 106 along the length; the A-folding section 104 is fixed with the semi-transparent and semi-reflective mirror 4 and the field lens 3; the B-folding section 105 is fixed with the total reflective mirror 2; the C-folding section 106 is provided with resting plate 5; the resting plate 5 is provided with a observation hole for collecting external images by the rear camera of the main smart phone 106.

The method for preparing the MR head-mounted mechanism comprises the steps of:

B1, folding the A-folding section and the B-folding section to a rhombic column, so that the lens is located at the connection line of the rhombic vertex; one side surface of the rhombic column is open and is an incident surface of image light, and the other three side surfaces are closed and form an observation hole wall, a semi-transparent semi-reflective mirror wall and a total reflective mirror wall respectively; the incident surface of image light faces the total reflective mirror wall; the total reflective mirror wall is provided with the total reflective mirror; the observation hole locates at the observation hole wall; the side wall of the rhombic column facing the observation hole is the semi-transparent semi-reflective mirror; the semi-transparent semi-reflective mirror locates at the semi-transparent semi-reflective mirror wall;

B2, expanding a light shield 6 at the A-folding section and inserting the light shield 6 into the observation hole wall;

B3, expanding the C-folding section and putting the main smart phone having rear camera on the resting plate, so that the rear camera aligns to the observation hole of the resting plate; folding the C-folding section then to the incident surface of light image of the rhombic column; the observation end includes the observation hole 102, at which the mixed reality image formed by mixing the screen image of the phone with the external image can be seen when the main smart phone displays the VR split screen mode image in the form of transverse double-split screen.

The bottom of the resting plate 5 is configured with a damper 7; the resting plate is detachably coupled to the housing via velcro tapes or buckles; the resting plate is fixedly coupled to the housing.

In another technical solution of the present invention, the MR calculation module is a main smart phone; the display assembly is a display module of the main smart phone; the IMU assembly comprises a magnetometer, a gyroscope and an accelerometer; the IMU assembly has a main IMU assembly and zero or more auxiliary IMU assemblies; the main IMU assembly collects the posture data of the display assembly and the main IMU assembly is arranged in the main smart phone; the auxiliary IMU assembly is arranged in one or more control devices wirelessly connected to the main smart phone; the auxiliary IMU assembly collects the posture data or position data of the one or more control devices; the posture data includes posture angle, angular rate or acceleration data; the imaging assembly comprises a main imaging assembly and a auxiliary imaging assembly; the main imaging assembly is a rear camera of the main smart phone, and the auxiliary imaging assembly is a camera at the control device and is optional.

The MR optical path module is a passive MR head-mounted mechanism; the main smart phone is fixed at the MR head-mounted mechanism; the main imaging assembly is the rear camera of the main smart phone; the control device is either a game console handle, a wearable device that can be worn on the hand or the foot, a sensor and a control device that are fixed at the MR head-mounted mechanism, or an auxiliary phone that is held by the user or is tied to the limbs of the user.

The virtual-image optical path of the MR head-mounted mechanism comprises a resting plate, a total reflection mirror and a field lens; the field lens is composed of two Fresnel lenses; herein the main smart phone is placed horizontally on the resting plate; the main smart phone displays the VR split-screen mode image in the form of double-split screen in the transverse direction when the MR head-mounted mechanism is working; image light of double-split screen then is reflected by means of the total reflection mirror onto the two Fresnel lens, which then refracts image light of double-split screen, so that image light forms two virtual-image light paths with preset viewing angle; virtual-image light is reflected by means of the virtual-image introduction surface onto an observation end, and real environment light is transmitted to the observation end by means of the real-image introduction surface, being mixed with the virtual image to form a mixed reality image.

The orientation of the rear camera of the main smart phone is the orientation of the MR head-mounted mechanism; the posture data of the display assembly is the posture data of the main smart phone; the IMU assembly at the main smart phone collects the posture data of the main smart phone; when the MR head-mounted mechanism is in operation, the rear camera of the main smart phone collects feature points of the real scene at the initial orientation of the MR head-mounted mechanism, and successively collects images as posture images of feature points while the MR head-mounted mechanism is in operation; the MR calculation module calculates the space position of the main smart phone according to the variation of the feature points at the posture image and the variation of the posture data of the main smart phone, and adjusts the images on the double-split screen based on the space position.

The image displayed in the form of transverse double-split screen comprises a virtual character and a control identifier; the MR calculation module generates the space position of the control identifier according to the posture data and position data of the control device uploaded by the auxiliary IMU assembly or the auxiliary imaging assembly; the control identifier moves with the movement of the control device; the virtual character can interact with the control identifier.

The main smart phone is connected to a external device by network; the virtual character and the control identifier included in the image that is displayed in the form of transverse double-split screen is a part of the mixed reality image; the virtual character corresponds to the external device, and when the virtual character interact with the control identifier, the external device performs respectively according to the interaction content.

The imaging method sequentially includes the steps of:

A1, the user fixes the main smart phone preinstalled with the MR application to the resting plate of the MR head-mounted mechanism and holds the auxiliary phone which is also a smart phone preinstalled with the MR application;

A2, the user wears the MR head-mounted mechanism, and brings the eyes close to the observation end to observe the mixed reality image;

A3, activating the MR application of the main smart phone and setting it as a display end; the main smart phone displays the image in the form of horizontal double-split screen, image light of double-split screen is reflected by means of the total reflection mirror onto the two Fresnel lenses, two Fresnel lenses refract image light of double-split screen, so that image light forms two virtual-image light paths with preset field angle; virtual-image light is reflected by means of the virtual-image introduction surface onto an observation end, and real environment light transmitted to the observation end by means of the real-image introduction surface, being mixed with the virtual image light to form a mixed reality image;

A4, the rear camera of the main smart phone collects feature points of the real scene at the initial orientation of the MR head-mounted mechanism, and successively collects images as posture images of feature points while the MR head-mounted mechanism is in operation; the MR calculation module calculates the space position of the main smart phone according to the variation of the feature points at the posture image and the variation of the posture data of the main smart phone, and adjusts the images on the double-split screen based on the space position;

A5, the user lifts the control device to a specific point of the mixed reality image, if the control device is a smart phone, activates the MR application on the auxiliary phone, and sets it as a control end; the auxiliary IMU assembly on the control device collects the posture data and position data of the auxiliary phone; the control end uploads the posture data and position data of the control device to the display end which is connected to the control end wirelessly;

A6, the MR calculation module generates the control identifier on the mixed reality image according to the posture data and position data of the auxiliary phone, wherein the control identifier moves with the movement of the auxiliary phone; when the control identifier on the mixed reality image is in contact with or adjacent to the virtual character, the virtual character interacts with the control identifier;

A7, the virtual character corresponds to the external device, and when the virtual character is interacting with the control identifier, the external device performs the corresponding implementation according to the interaction content.

The MR head-mounted mechanism is made up of a thin sheet, which is provided with an A-folding section, a B-folding section and a C-folding section along the length; the A-folding section is fixed with the semi-transparent and semi-reflective mirror and the field lens; the B-folding section is fixed with the total reflective mirror; the C-folding section is provided with resting plate; the resting plate is provided with a observation hole for collecting external images by the rear camera of the main smart phone.

The method for preparing the MR head-mounted mechanism comprises the steps of:

B1, folding the A-folding section and the B-folding section to a rhombic column, so that the lens is located at the connection line of the rhombic vertex; one side surface of the rhombic column is open and is an incident surface of image light, and the other three side surfaces are closed and form an observation hole wall, a semi-transparent semi-reflective mirror wall and a total reflective mirror wall respectively; the incident surface of image light faces the total reflective mirror wall; the total reflective mirror wall is provided with the total reflective mirror; the observation hole locates at the observation hole wall; the side wall of the rhombic column facing the observation hole is the semi-transparent semi-reflective mirror; the semi-transparent semi-reflective mirror locates at the semi-transparent semi-reflective mirror wall;

B2, expanding a light shield at the A-folding section and inserting the light shield into the observation hole wall;

B3, expanding the C-folding section and putting the main smart phone having rear camera on the resting plate, so that the rear camera aligns to the observation hole of the resting plate; folding the C-folding section then to the incident surface of light image of the rhombic column; the observation end includes the observation hole, at which the mixed reality image formed by mixing the screen image of the phone with the external image can be seen when the main smart phone displays the VR split screen mode image in the form of transverse double-split screen.

In this example, if the user needs to set a unified coordinate system's origin in the unified spatial position data shared by the main smart phone and the auxiliary smart phone, one of the possible methods is to make the main smart phone and the auxiliary smart phone collect an initial posture on the same target when the device is used initially, so as to identify and mark the feature points in the initial posture as the coordinate system's origin.

EXAMPLES

The MR application is installed onto the user's main smart phone and the auxiliary smart phone, and the main smart phone is fixed on the resting plate of the MR head-mounted mechanism, and the auxiliary smart phone is held in the hand.

After the user wears the MR head-mounted mechanism, the hand-held auxiliary smart phone functions as a controlling handle, and the auxiliary smart phone virtually maneuvers the displayed file icons in mixed reality.

Through the observation hole 102 and the semi-transparent semi-reflective mirror 4, the user directly reviews the real environment paper manuscript in mixed reality. The paper manuscript is associated with the file control icon, and the file control icon is associated with the corresponding computer file of the paper manuscript.

After the user has finished reviewing and finalizing the manuscript in mixed reality for printing, the user can then use the hand-held auxiliary smart phone to maneuver the file control icon directly onto the virtual printer icon in mixed reality. Since the virtual printer icon is associated with a real printer, the interaction of the file control icon with the virtual printer icon is equivalent to the user's official printing command, and the real printer in the office executes the print job directly.

What is claimed is:

1. An imaging method for modular mixed reality (MR) device, wherein
the MR device comprising: an MR calculation module, an MR optical path module, and an MR posture module;
the MR calculation module comprises a display assembly;
the MR posture module comprises an imaging assembly and an IMU assembly, and the imaging assembly is configured to collect images in a preset angular direction of the display assembly, and the IMU assembly is configured to collect posture data of the MR device;
the MR calculation module is connected to the MR posture module, adjusting display content of the display assembly according to the image data and posture data acquired by the MR posture module;
the MR optical path module comprises a virtual-image optical path and a mixed optical path, the virtual-image optical path being connected to the display assembly;
the input end of the mixed optical path is connected to the virtual-image optical path, while the output end of the mixed optical path is an observation end;
a semi-transparent semi-reflective mirror is configured in the mixed optical path;
one surface of the semi-transparent semi-reflective mirror is configured as a real-image introduction surface and the other surface of the semi-transparent semi-reflective mirror is configured as a virtual-image introduction surface;
the real-image introduction surface faces a real environment, while the virtual-image introduction surface faces the virtual-image optical path;
display content of the display assembly is processed and transmitted by means of the virtual-image optical path to form a virtual image;
virtual-image light is reflected by means of the virtual-image introduction surface onto the observation end, and real environment light is transmitted to the observation end by means of the real-image introduction surface, being mixed with the virtual image to form a mixed reality image,
wherein the MR calculation module is a main smart phone,
the display assembly is a display module of the main smart phone;

the IMU assembly comprises a magnetometer, a gyroscope and an accelerometer;
the IMU assembly has a main IMU assembly and an auxiliary IMU assembly;
the main IMU assembly collects the posture data of the display assembly;
the main IMU assembly is arranged in the main smart phone;
the auxiliary IMU assembly is arranged in one or more control devices wirelessly connected to the main smart phone;
the auxiliary IMU assembly collects the posture data or position data of the one or more control devices;
the posture data includes posture angle, angular rate or acceleration data;
the imaging assembly comprises a main imaging assembly and an auxiliary imaging assembly;
the main imaging assembly is a rear camera of the main smart phone, and the auxiliary imaging assembly is a camera arranged at the control device,
the semi-transparent semi-reflective mirror is configured to
receive, when the MR optical path module is worn by a user, the virtual-image light from a first direction above a horizontal line of sight of the user, and
reflect the virtual-image light toward the observation end, and
the MR optical path module is a passive MR head-mounted mechanism including an opening opened toward a second direction to receive the main smart phone, the second direction crossing the first direction.

2. The imaging method for modular mixed reality (MR) device as claimed in claim 1, wherein:
the main smart phone is fixed at the passive MR head-mounted mechanism; and
the control device is either a game console handle, a wearable device that can be worn on the hand or the foot, a sensor and a control device that are fixed at the passive MR head-mounted mechanism, or an auxiliary phone that is held by the user or is tied to the limbs of the user.

3. The imaging method for modular mixed reality (MR) device as claimed in claim 2, wherein:
the virtual-image optical path of the passive MR head-mounted mechanism comprises a resting plate, a total reflection mirror and a field lens;
the field lens is combined by two Fresnel lenses;
the main smart phone is placed horizontally on the resting plate;
the main smart phone displays the VR split-screen mode image in the form of a horizontal double-split screen when the passive MR head-mounted mechanism is in operation;
the image light of the horizontal double-split screen is reflected by means of the total reflection mirror onto the two Fresnel lenses, which then refract image light of the horizontal double-split screen, so that image light forms two virtual-image light paths with preset field angle.

4. The imaging method for modular mixed reality (MR) device as claimed in claim 3, wherein:
the orientation of the rear camera of the main smart phone is the orientation of the passive MR head-mounted mechanism;
the posture data of the display assembly is the posture data of the main smart phone;
the IMU assembly at the main smart phone collects the posture data of the main smart phone;
when the passive MR head-mounted mechanism is in operation, the rear camera of the main smart phone collects feature points of the real scene at the initial orientation of the passive MR head-mounted mechanism, and successively collects images as posture images while the passive MR head-mounted mechanism is in operation;
the MR calculation module adjusts the images on the horizontal double-split screen according to the variation of the feature points at the posture image and the variation of the posture data of the main smart phone.

5. The imaging method for modular mixed reality (MR) device as claimed in claim 4, wherein:
the image displayed in the form of the horizontal double-split screen comprises a virtual character and a control identifier;
the MR calculation module generates the control identifier according to the posture data and the position data of the control device uploaded by the auxiliary IMU assembly;
the control identifier moves with the movement of the control device;
the virtual character can interact with the control identifier.

6. The imaging method for modular mixed reality (MR) device as claimed in claim 5, wherein:
the main smart phone is connected to an external device by network;
the virtual character and the control identifier included in the image that is displayed in the form of the horizontal double-split screen is a part of the mixed reality image;
the virtual character corresponds to the external device, and when the virtual character interacts with the control identifier, the external device performs respective implementation according to the interaction content.

7. The imaging method for modular mixed reality (MR) device as claimed in claim 6, wherein the imaging method sequentially includes the steps of:
A1, the user fixing the main smart phone preinstalled with the MR application to the resting plate of the passive MR head-mounted mechanism and holding the auxiliary phone which is also a smart phone preloaded the MR application;
A2, the user wearing the passive MR head-mounted mechanism, and bringing the eyes close to the observation end so as to observe the mixed reality image;
A3, activating the MR application of the main smart phone and setting it as a display end; the main smart phone displaying the image in the form of a horizontal double-split screen, image light of the horizontal double-split screen is reflected by means of the total reflection mirror onto the two Fresnel lenses, two Fresnel lenses refract image light of the horizontal double-split screen, so that image light forms two virtual-image light paths with preset field angle; virtual-image light is reflected by means of the virtual-image introduction surface onto an observation end, and real environment light transmitted to the observation end by means of the real-image introduction surface, being mixed with the virtual image light to form a mixed reality image;
A4, the rear camera of the main smart phone collecting feature points of the real scene at the initial orientation of the passive MR head-mounted mechanism, and successively collecting images as posture images while the passive MR head-mounted mechanism is in operation; the MR calculation module adjusting the images on the horizontal double-split screen according to the variation of the feature points at the posture image and the variation of the posture data of the main smart phone;

A5, the user lifting the auxiliary mobile phone to a specific point of the mixed reality image, and activating the MR application on the auxiliary phone and setting it as a control end; the auxiliary IMU assembly on the auxiliary phone collecting the posture data and the position data of the auxiliary phone; the control end uploading the posture data and position data of the auxiliary phone to the display end which is connected to the control end by wirelessly manners;

A6, the MR calculation module generating the control identifier on the mixed reality image according to the posture data and position data of the auxiliary phone, wherein the control identifier moves with the movement of the auxiliary phone; when the control identifier on the mixed reality image is in contact with or adjacent to the virtual character, the virtual character interacts with the control identifier;

A7, the virtual character corresponds to the external device, and when the virtual character is interacting with the control identifier, the external device performs corresponding implementation according to the interaction content.

8. The imaging method for modular mixed reality (MR) device as claimed in claim 7, further comprising a monocular visual inertial odometer method comprising the steps of:

B1, the main smart phone and the auxiliary phone collecting images by means of cameras to generate posture image respectively; the main smart phone and the auxiliary phone collecting posture data by means of built-in IMU assembly respectively; the main smart phone and the auxiliary phone associate the posture image with the posture data respectively, forming a respective spatial image association data; the main smart phone and the auxiliary phone aggregate respective spatial image related data through network connection to generate a unified spatial image related database in the main smart phone and the auxiliary phone;

B2, the main smart phone and the auxiliary phone successively collecting posture images and posture data during the movement, and adding the collected posture images and posture data to the spatial image related database respectively to associate;

B3, during the movement, the main smart phone and the auxiliary phone comparing the collected posture images and the posture data with that data in the spatial image related database to obtain the exact location of the phone in the current space and predict the trajectory and posture change of the phone;

B4, the main smart phone and the auxiliary phone reading the spatial image related database during the movement, and comparing the collected posture images with the posture images and the posture data in the past N time frames collected from the same coordinate and same posture, updating the spatial image related database when there is difference between the collected posture images and the posture images and the posture data in the past N time frames;

B5, in steps B3 and B4, the main smart phone and the auxiliary phone comparing and verifying the data with a preset tolerance threshold to improve the efficiency and robustness of the spatial location.

9. An imaging method for modular mixed reality (MR) device, wherein the MR device comprising: an MR calculation module, an MR optical path module, and an MR posture module;

the MR calculation module comprises a display assembly;

the MR posture module comprises an imaging assembly and an IMU assembly, and the imaging assembly is configured to collect images in a preset angular direction of the display assembly, and the IMU assembly is configured to collect posture data of the MR device;

the MR calculation module is connected to the MR posture module, adjusting display content of the display assembly according to the image data and posture data acquired by the MR posture module;

the MR optical path module comprises a virtual-image optical path and a mixed optical path, the virtual-image optical path being connected to the display assembly;

the input end of the mixed optical path is connected to the virtual-image optical path, while the output end of the mixed optical path is an observation end;

a semi-transparent semi-reflective mirror is configured in the mixed optical path;

one surface of the semi-transparent semi-reflective mirror is configured as a real-image introduction surface and the other surface of the semi-transparent semi-reflective mirror is configured as a virtual-image introduction surface;

the real-image introduction surface faces a real environment, while the virtual-image introduction surface faces the virtual-image optical path;

display content of the display assembly is processed and transmitted by means of the virtual-image optical path to form a virtual image;

virtual-image light is reflected by means of the virtual-image introduction surface onto the observation end, and real environment light is transmitted to the observation end by means of the real-image introduction surface, being mixed with the virtual image to form a mixed reality image, the MR calculation module is a main smart phone, the display assembly is a display module of the main smart phone;

the IMU assembly comprises a magnetometer, a gyroscope and an accelerometer;

the IMU assembly has a main IMU assembly and an auxiliary IMU assembly;

the main IMU assembly collects the posture data of the display assembly;

the main IMU assembly is arranged in the main smart phone;

the auxiliary IMU assembly is arranged in one or more control devices wirelessly connected to the main smart phone;

the auxiliary IMU assembly collects the posture data or position data of the one or more control devices;

the posture data includes posture angle, angular rate or acceleration data;

the imaging assembly comprises a main imaging assembly and an auxiliary imaging assembly;

the main imaging assembly is a rear camera of the main smart phone, and the auxiliary imaging assembly is a camera arranged at the control device, the semi-transparent semi-reflective mirror is configured to
receive, when the MR optical path module is worn by a user, the virtual-image light from a direction above a horizontal line of sight of the user, and
reflect the virtual-image light toward the observation end, the MR optical path module is a passive MR head-mounted mechanism;

the main smart phone is fixed at the passive MR head-mounted mechanism;

the control device is either a game console handle, a wearable device that can be worn on the hand or the foot, a sensor and a control device that are fixed at the passive MR head-mounted mechanism, or an auxiliary phone that is held by the user or is tied to the limbs of the user, the virtual-image optical path of the passive MR head-mounted mechanism comprises a resting plate, a total reflection mirror and a field lens;

the field lens is combined by two Fresnel lenses;

the main smart phone is placed horizontally on the resting plate;

the main smart phone displays the VR split-screen mode image in the form of a horizontal double-split screen when the passive MR head-mounted mechanism is in operation;

the image light of the horizontal double-split screen is reflected by means of the total reflection mirror onto the two Fresnel lenses, which then refract image light of the horizontal double-split screen, so that image light forms two virtual-image light paths with preset field angle, the orientation of the rear camera of the main smart phone is the orientation of the passive MR head-mounted mechanism;

the posture data of the display assembly is the posture data of the main smart phone;

the IMU assembly at the main smart phone collects the posture data of the main smart phone;

when the passive MR head-mounted mechanism is in operation, the rear camera of the main smart phone collects feature points of the real scene at the initial orientation of the passive MR head-mounted mechanism, and successively collects images as posture images while the passive MR head-mounted mechanism is in operation;

the MR calculation module adjusts the images on the horizontal double-split screen according to the variation of the feature points at the posture image and the variation of the posture data of the main smart phone, the passive MR head-mounted mechanism is made up of a sheet, which is provided with an A-folding section, a B-folding section and a C-folding section along the length; the A-folding section is fixed with the semi-transparent and semi-reflective mirror and the field lens; the B-folding section is fixed with the total reflective mirror; the C-folding section is provided with resting plate; the resting plate is provided with an observation hole for collecting external images by the rear camera of the main smart phone; the method for preparing the passive MR head- mounted mechanism comprises the steps of:

B1, folding the A-folding section and the B-folding section to a rhombic column, so that the lens is located at the connection line of the rhombic vertex; one side surface of the rhombic column is open and is an incident surface of image light, and the other three side surfaces are closed and form an observation hole wall, a semi-transparent semi-reflective mirror wall and a total reflective mirror wall respectively; the incident surface of image light faces the total reflective mirror wall; the total reflective mirror wall is provided with the total reflective mirror; the observation hole locates at the observation hole wall; the side wall of the rhombic column facing the observation hole is the semi-transparent semi-reflective mirror; the semi-transparent semi-reflective mirror locates at the semi-transparent semi-reflective mirror wall;

B2, expanding a light shield at the A-folding section and inserting the light shield into the observation hole wall; and B3, expanding the C-folding section and putting the main smart phone having rear camera on the resting plate, so that the rear camera aligns to the observation hole of the resting plate; folding the C-folding section then to the incident surface of light image of the rhombic column; the observation end includes the observation hole, at which the mixed reality image formed by mixing the screen image of the phone with the external image can be seen when the main smart phone displays the VR split screen mode image in the form of the horizontal double-split screen.

10. The imaging method for modular mixed reality (MR) device as claimed in claim 1, wherein the main smart phone is fixed at the passive MR head-mounted mechanism;

the main imaging assembly is the rear camera of the main smart phone;

the control device is either a game console handle, a wearable device that can be worn on the hand or the foot, a sensor and a control device that are fixed at the passive MR head-mounted mechanism, or an auxiliary phone that is held by the user or is tied to the limbs of the user.

11. The imaging method for modular mixed reality (MR) device as claimed in claim 10, wherein the virtual-image optical path of the passive MR head-mounted mechanism comprises a resting plate, a total reflection mirror and a field lens;

the field lens is combined by two Fresnel lenses;

the main smart phone is placed horizontally on the resting plate;

the main smart phone displays the VR split-screen mode image in the form of the horizontal double-split screen in the horizontal direction when the passive MR head-mounted mechanism is in operation;

image light of the horizontal double-split screen is reflected by means of the total reflection mirror onto the two Fresnel lenses, which then refract image light of the horizontal double-split screen, so that image light forms two virtual-image light paths with preset field angle;

virtual-image light is reflected by means of the virtual-image introduction surface onto an observation end, and real environment light is transmitted to the observation end by means of the real-image introduction surface, being mixed with the virtual image light to form a mixed reality image.

12. The imaging method for modular mixed reality (MR) device as claimed in claim 11, wherein the orientation of the rear camera of the main smart phone is the orientation of the passive MR head-mounted mechanism;

the posture data of the display assembly is the posture data of the main smart phone;

the IMU assembly at the main smart phone collects the posture data of the main smart phone;

when the passive MR head-mounted mechanism is in operation, the rear camera of the main smart phone collects feature points of the real scene at the initial orientation of the passive MR head-mounted mechanism, and successively collects images as posture images of feature points while the passive MR head-mounted mechanism is in operation;

the MR calculation module calculates the space position of the main smart phone according to the variation of the feature points at the posture image and the variation of the posture data of the main smart phone, and adjusts the images on the horizontal double-split screen based on the space position.

13. The imaging method for modular mixed reality (MR) device as claimed in claim 12, wherein the image displayed in the form of the horizontal double-split screen comprises a virtual character and a control identifier;

the MR calculation module generates the space position of the control identifier according to the posture data and position data of the control device uploaded by the auxiliary IMU assembly or the auxiliary imaging assembly;

the control identifier moves with the movement of the control device;

the virtual character can interact with the control identifier.

14. The imaging method for modular mixed reality (MR) device as claimed in claim 13, wherein the main smart phone is connected to an external device by network;

the virtual character and the control identifier included in the image that is displayed in the form of the horizontal double-split screen is a part of the mixed reality image;

the virtual character corresponds to the external device, and when the virtual character interacts with the control identifier, the external device performs respective implementation according to the interaction content.

15. The imaging method for modular mixed reality (MR) device as claimed in claim 14, wherein the imaging method sequentially includes the steps of:

A1, the user fixing the main smart phone preinstalled with the MR application to the resting plate of the passive MR head-mounted mechanism and holding the auxiliary phone which is also a smart phone preloaded the MR application;

A2, the user wearing the passive MR head-mounted mechanism, and bringing the eyes close to the observation end so as to observe the mixed reality image;

A3, activating the MR application of the main smart phone and setting it as a display end;

the main smart phone displaying the image in the form of the horizontal double-split screen, image light of double-split screen is reflected by means of the total reflection mirror onto the two Fresnel lenses, two Fresnel lenses refract image light of the horizontal double-split screen, so that image light forms two virtual-image light paths with preset field angle; virtual-image light is reflected by means of the virtual-image introduction surface onto an observation end, and real environment light transmitted to the observation end by means of the real-image introduction surface, being mixed with the virtual image light to form a mixed reality image;

A4, the rear camera of the main smart phone collecting feature points of the real scene at the initial orientation of the passive MR head-mounted mechanism, and successively collecting images as posture images of feature points while the passive MR head-mounted mechanism is in operation; the MR calculation module calculating the space position of the main smart phone according to the variation of the feature points at the posture image and the variation of the posture data of the main smart phone, and adjusting the images on the horizontal double-split screen based on the space position;

A5, the user lifting the control device to a specific point of the mixed reality image, if the control device is a smart phone, activating the MR application on the auxiliary phone and setting it as a control end; the auxiliary IMU assembly on the control device collecting the posture data and position data of the auxiliary phone; the control end uploading the posture data and position data of the control device to the display end which is connected to the control end wirelessly;

A6, the MR calculation module generating the control identifier on the mixed reality image according to the posture data and position data of the auxiliary phone, wherein the control identifier moves with the movement of the auxiliary phone; when the control identifier on the mixed reality image is in contact with or adjacent to the virtual character, the virtual character interacts with the control identifier;

A7, the virtual character corresponds to the external device, and when the virtual character is interacting with the control identifier, the external device performs corresponding implementation according to the interaction content.

16. The imaging method for modular mixed reality (MR) device as claimed in claim 12, wherein the passive MR head-mounted mechanism is made up of a sheet, which is provided with an A-folding section, a B-folding section and a C-folding section along the length;

the A-folding section is fixed with the semi-transparent and semi-reflective mirror and the field lens;

the B-folding section is fixed with the total reflective mirror;

the C-folding section is provided with resting plate;

the resting plate is provided with an observation hole for collecting external images by the rear camera of the main smart phone.

17. The imaging method for modular mixed reality (MR) device as claimed in claim 16, wherein the method for preparing the passive MR head-mounted mechanism comprises the steps of:

B1, folding the A-folding section and the B-folding section to a rhombic column, so that the lens is located at the connection line of the rhombic vertex; one side surface of the rhombic column is open and is an incident surface of image light, and the other three side surfaces are closed and form an observation hole wall, a semi-transparent semi-reflective mirror wall and a total reflective mirror wall respectively; the incident surface of image light faces the total reflective mirror wall; the total reflective mirror wall is provided with the total reflective mirror; the observation hole locates at the observation hole wall; the side wall of the rhombic column facing the observation hole is the semi-transparent semi-reflective mirror; the semi-transparent semi-reflective mirror locates at the semi-transparent semi-reflective mirror wall;

B2, expanding a light shield at the A-folding section and inserting the light shield into the observation hole wall;

B3, expanding the C-folding section and putting the main smart phone having rear camera on the resting plate, so that the rear camera aligns to the observation hole of the resting plate; folding the C-folding section then to the incident surface of light image of the rhombic column; the observation end includes the observation hole, at which the mixed reality image formed by mixing the screen image of the phone with the external image can be seen when the main smart phone displays the VR split screen mode image in the form of the horizontal double-split screen.

18. The imaging method for modular mixed reality (MR) device as claimed in claim 1, wherein
the passive MR head-mounted mechanism includes
a housing, and
a resting plate coupled to the housing and configured to support the main smart phone, wherein the resting plate includes a bottom configured to support the main smart phone, and a side facing the housing, and
the housing, the bottom of the resting plate, and the side of the resting plate define the opening opened toward the second direction.

19. The imaging method for modular mixed reality (MR) device as claimed in claim 18, wherein
the resting plate is fixedly coupled to the housing at the bottom and detachably coupled to the housing at an upper portion of the resting plate.

* * * * *